United States Patent
Clements et al.

(10) Patent No.: US 9,360,469 B1
(45) Date of Patent: Jun. 7, 2016

(54) MULTIWELL MICROELECTRODE ARRAY WITH OPTICAL STIMULATION

(71) Applicant: Axion BioSystems, Inc., Atlanta, GA (US)

(72) Inventors: Isaac Perry Clements, Marietta, GA (US); Amanda Jervis Preyer, Atlanta, GA (US); Swaminathan Rajaraman, Decatur, GA (US); Daniel Christopher Millard, Atlanta, GA (US); James David Ross, Decatur, GA (US)

(73) Assignee: Axion BioSystems, Inc., Atlanta, GA (US)

( * ) Notice: Subject to any disclaimer, the term of this patent is extended or adjusted under 35 U.S.C. 154(b) by 0 days.

(21) Appl. No.: 15/041,589

(22) Filed: Feb. 11, 2016

Related U.S. Application Data

(63) Continuation of application No. 14/738,618, filed on Jun. 12, 2015, now Pat. No. 9,279,797.

(60) Provisional application No. 62/011,291, filed on Jun. 12, 2014.

(51) Int. Cl.
*G01N 21/01* (2006.01)
*G01N 33/483* (2006.01)

(52) U.S. Cl.
CPC ............ *G01N 33/4836* (2013.01); *G01N 21/01* (2013.01); *G01N 2021/015* (2013.01); *G01N 2201/0446* (2013.01); *G01N 2201/062* (2013.01)

(58) Field of Classification Search
CPC ....... G01N 21/62; G01N 21/63; G01N 21/64; G01N 21/01; G01N 2021/0106; G01N 2021/015; G01N 2021/0156
See application file for complete search history.

(56) References Cited

U.S. PATENT DOCUMENTS

| | | | |
|---|---|---|---|
| 6,043,880 A | 3/2000 | Andrews et al. |
| 6,347,250 B1 | 2/2002 | Nisch et al. |
| 6,372,485 B1 | 4/2002 | Clark et al. |
| 6,692,250 B1 | 2/2004 | Decaudin et al. |
| 7,341,362 B2 | 3/2008 | Bjornson et al. |
| 7,981,362 B2 | 7/2011 | Glezer et al. |

(Continued)

FOREIGN PATENT DOCUMENTS

| | | |
|---|---|---|
| WO | 2013033080 A1 | 3/2013 |
| WO | 2014067963 | 5/2014 |

OTHER PUBLICATIONS

Abilez, Oscar, "Optogenetic LED Array for Perturbing Cardiac Electrophysiology", 35th Annual International Conference of the IEEE.

(Continued)

*Primary Examiner* — Alexander Noguerola
(74) *Attorney, Agent, or Firm* — Meunier Carlin & Curfman LLC

(57) ABSTRACT

An electro-optical stimulation and recording system is disclosed, including a substrate and a plurality of wells coupled to the substrate. The system also includes at least one electrode set disposed proximate a respective one of the plurality of wells, wherein the electrode set comprises at least one electrode configured to collect an electric signal associated with at least a portion of the respective well. The system also includes a light-emitting element set corresponding to a respective one of the wells and configured to deliver optical stimulation to at least a portion of the respective well.

2 Claims, 18 Drawing Sheets

(56) References Cited

U.S. PATENT DOCUMENTS

| | | | |
|---|---|---|---|
| 2002/0113213 A1 | 8/2002 | Amirkhanian et al. | |
| 2003/0049688 A1 | 3/2003 | Michnick et al. | |
| 2003/0162288 A1* | 8/2003 | Everett | A01G 7/04 435/292.1 |
| 2004/0022677 A1 | 2/2004 | Wohlstadter et al. | |
| 2007/0211460 A1 | 9/2007 | Ravkin | |
| 2007/0281322 A1 | 12/2007 | Jaffe et al. | |
| 2008/0207465 A1 | 8/2008 | Ravkin et al. | |
| 2009/0032743 A1* | 2/2009 | Schirr | G01N 21/6452 250/578.1 |
| 2012/0064564 A1 | 3/2012 | Grassl et al. | |
| 2012/0182556 A1* | 7/2012 | Van Praet | G01N 21/253 356/440 |
| 2012/0295376 A1 | 11/2012 | Lee et al. | |
| 2013/0330816 A1 | 12/2013 | Deisseroth et al. | |
| 2015/0289778 A1 | 10/2015 | Ohl et al. | |

OTHER PUBLICATIONS

Bugaj, Lukasz, et al., "Optogenetic protein clustering and signaling activation in mammalian cells", Nature Methods, vol. 10, No. 3, 2013.

Bugaj, Lukasz, et al., Supplementary Information.

El Hady, Ahmed, et al., "Optogenetic stimulation effectively enhances intrinsically generated network synchrony", Frontiers in Neural Circuits, Article 167, vol. 7, 2013.

Lignani, Gabriele, et al., "Long-term optical stimulation of channelrhodopsin-expressing neurons to study network plasticity", Frontiers in Molecular Neuroscience, Article 22, vol. 6, 2013.

Tchumatchenko, Tatjana, et al., "Delivery of continuously-varying stimuli using channelrhodopsin-2", Frontiers in Neural Circuits, Article 184, vol. 7, 2013.

International Search Report and Written Opinion, mailed Nov. 13, 2015, in connection with International Application No. PCT/US2015/35677.

* cited by examiner

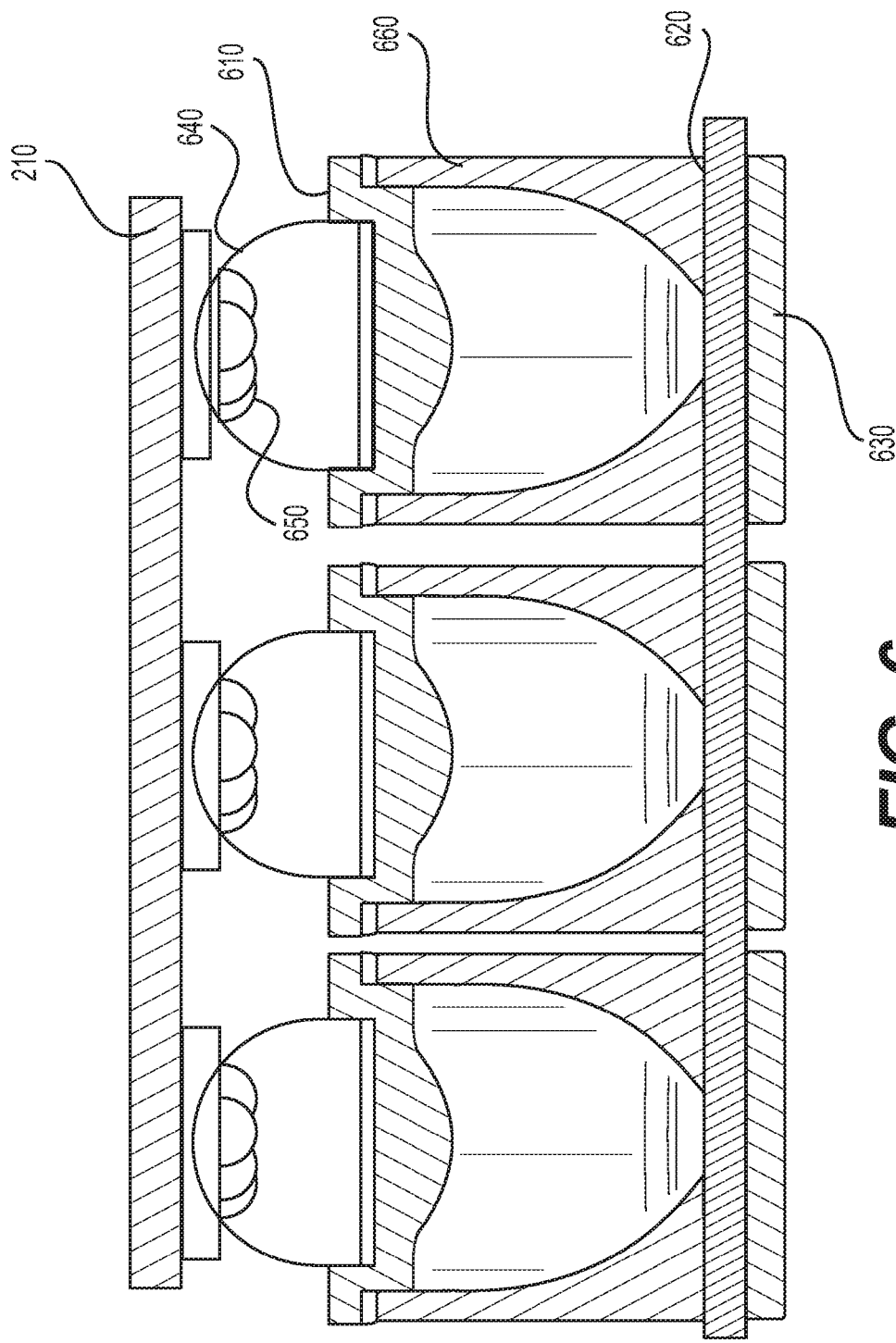

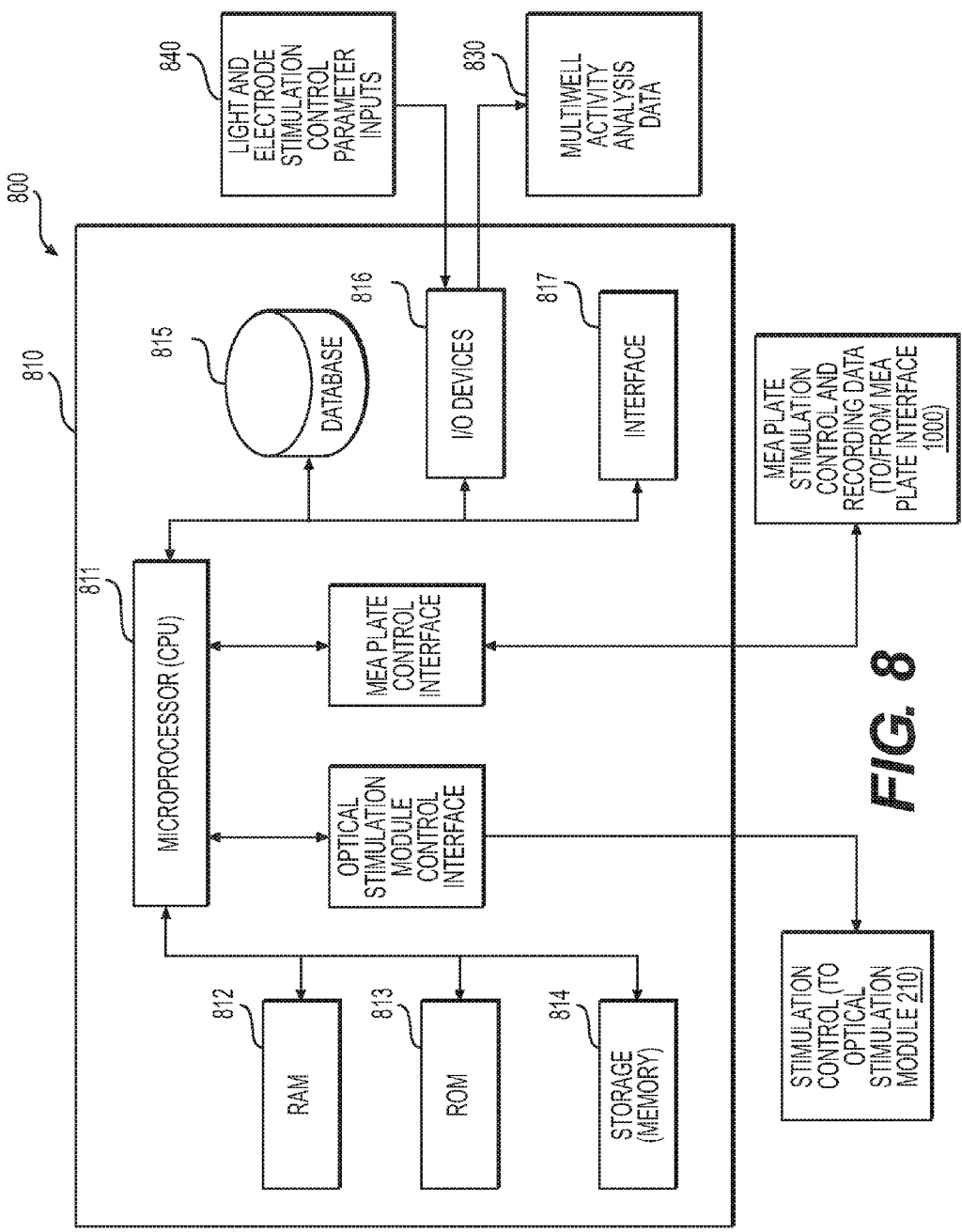

MULTIWELL MICROELECTRODE ARRAY WITH OPTICAL STIMULATION

CROSS REFERENCE TO RELATED APPLICATIONS

This application is a continuation of U.S. patent application Ser. No. 14/738,618, filed on Jun. 12, 2015, entitled "MULTIWELL MICROELECTRODE ARRAY WITH OPTICAL STIMULATION," which claims the benefit of U.S. Provisional Patent Application No. 62/011,291, filed on Jun. 12, 2014, entitled "MULTIWELL MICROELECTRODE ARRAY WITH OPTICAL STIMULATION," the disclosures of which are expressly incorporated herein by reference in their entireties.

TECHNICAL FIELD

The present disclosure relates generally to tools for facilitating optogenetic stimulation of cells and tissue and, more particularly, to multiwell microelectrode arrays with optical stimulation capabilities and associated methods for using the same.

BACKGROUND

Microelectrode arrays (MEAs) are an invaluable tool for scientific discovery and medical research. Because they can actively monitor and manipulate cellular activity (at both the single-cell and tissue levels) using electrical stimulation/recording, MEAs provide extraordinary insight into cell network interactions. Many conventional MEAs are of the single-well variety, meaning that only a single cell or tissue culture may be tested/analyzed at a time. Consequently, testing of multiple cell or tissue samples using conventional single-well microplates typically requires a significant monetary investment in multiple single-well measurement test beds, a significant allocation of time to sequentially test each cell or tissue sample, or some combination of the two.

To provide a more cost- and time-efficient platform for simultaneously testing multiple cell or tissue cultures, multiwell MEAs were developed. Unlike their single-well counterparts, multiwell MEAs provide an array of culture wells, each of which has a corresponding array of electrodes for recording electrical activity from (and/or delivering electrical stimulation to) the contents of the well. Current multiwell MEAs come in a variety of sizes, including, 4-, 12-, 24-, 48-, 72-, 96-, and 384-well configurations, providing a significant number of options for scaling in vitro testing to meet the needs of most any experimental setting. Although multiwell MEAs have certainly alleviated the scalability problems associated with single-well MEAs, they are generally limited in their ability to deliver different modes of stimulation (e.g., electrical, optical, thermal, etc.)

More specifically, despite the relative success of multiwell MEA systems, the technology's impact may be limited by the inherent limitations of electrical stimulation. Electrical stimulation pulses from MEA microelectrodes are limited to the locations of the electrodes and excite all nearby electroactive cells, regardless of cell sub-type. Electrically mediated inhibition of cell activity requires complex stimulation paradigms that are impractical and unreliable. Additionally, the amount of charge injection required for extracellular stimulation can saturate sensitive electronics and leave residual charge on the electrodes. In turn, this charge creates blind spots in electrical recordings that obscure critical activity around the time of stimulation. Therefore, there is a need for new stimulation solutions that can more selectively control cell networks without creating distortions or artifacts in the electrophysiological recordings.

Optogenetic stimulation techniques provide a more selective mechanism for manipulating cell cultures. In optogenetics methodologies, selected cells are genetically manipulated to express light sensitive membrane proteins called opsins. Specific cell types within heterogeneous cultures can then be genetically targeted for activation or inhibition with light of specific wavelengths. This light can be precisely pulsed and more evenly delivered across cultures, stimulating (or inhibiting) only the targeted cell types, while creating minimal stimulation artifact. Using different methodologies, optogenetic stimulation can alternatively provide the capability to influence intracellular signaling.

In order to provide a multiwell MEA solution with enhanced capability for selectively targeting different types of cells within a culture or tissue sample, a multiwell MEA system with integrated, independently controllable optical stimulation capabilities would be advantageous. The presently disclosed multiwell microelectrode arrays with integrated optical stimulation capabilities and associated methods for using the same are directed to overcoming one or more of the problems set forth above and/or other problems in the art.

SUMMARY

According to one aspect, the present disclosure is directed to an electro-optical stimulation and recording system, comprising a substrate and a plurality of wells coupled to the substrate. The multiwell plate may also include one or more electrode sets, each electrode set disposed proximate a respective one of the plurality of wells. Each electrode set comprises at least one electrode configured to collect an electric signal associated with at least a portion of the respective well. The multiwell plate may also include at least one light-emitting element set corresponding to a respective one of the wells and configured to deliver optical stimulation to at least a portion of the respective well.

In accordance with another aspect, the present disclosure is directed to a method for large-scale in vitro testing or manipulation of cell cultures. The method may comprise providing a control signal for causing a light-emitting element to emit light in an illumination pattern, the light-emitting element disposed proximate a well of a multiwell plate. The method may also comprise detecting, via an electrode disposed proximate the well, a signal associated with at least a portion of the well. The method may also comprise analyzing the detected signal and outputting information indicative of the analysis. The method may also comprise comparing the detected signal with benchmark data. The method may also comprise determining, based on the comparison, that adjustment of the illumination pattern is required. The method may also comprise modifying one the illumination pattern based on the determination. The detected signals may be analyzed, and information indicative of the analysis may be output, via a user interface element on a display. Optical stimulation parameters may be automatically adjusted based on detected signals, on a per well basis. Such automatic, algorithmic adjustment may be useful, for example, to optimally adjust light patterns on a per well basis. Software tools may allow light patterns to be generated and directed to selected wells and provide visualization of delivered light alongside visualizations of detected electrical activity.

In accordance with another aspect, the present disclosure is directed to a an electro-optical stimulation and recording system, comprising an electrode set disposed proximate a first well and comprising a first electrode configured to collect an electric signal associated with at least a portion of the first well. The system may also comprise a first light-emitting element set configured to deliver optical stimulation to at least a portion of the first well; and a processor. The processor may be configured to provide a first control signal for causing the first light-emitting element to emit light at a first illumination pattern; and detect, via the first electrode, a first signal associated with at least a portion of the respective well.

In another example embodiment, the present disclosure is directed to an optical stimulation system comprising a microplate having a plurality of well. The system may also comprise at least one light-emitting element set corresponding to at least one of the plurality of wells and configured to deliver optical stimulation to at the at least one well. The system may also comprise a lid configured to couple to the microplate, wherein the lid enhances delivery of light through the lid via at least one of recesses, lenses, and reflective surfaces.

BRIEF DESCRIPTION OF THE DRAWINGS

FIG. 6 provides a schematic block diagram of a cross-section of another embodiment of multiwell microelectrode array (MEA) with a detachable optical stimulation module coupled to the MEA, consistent with certain disclosed embodiments.

FIG. 8 provides a block diagram of a processor-based computing system having an integrated data analysis and control suite that is used to control and conduct various experiments using the presently disclosed multiwell microelectrode array (MEA) with optical stimulation capabilities, in accordance with certain disclosed embodiments.

DETAILED DESCRIPTION

Figure 1:
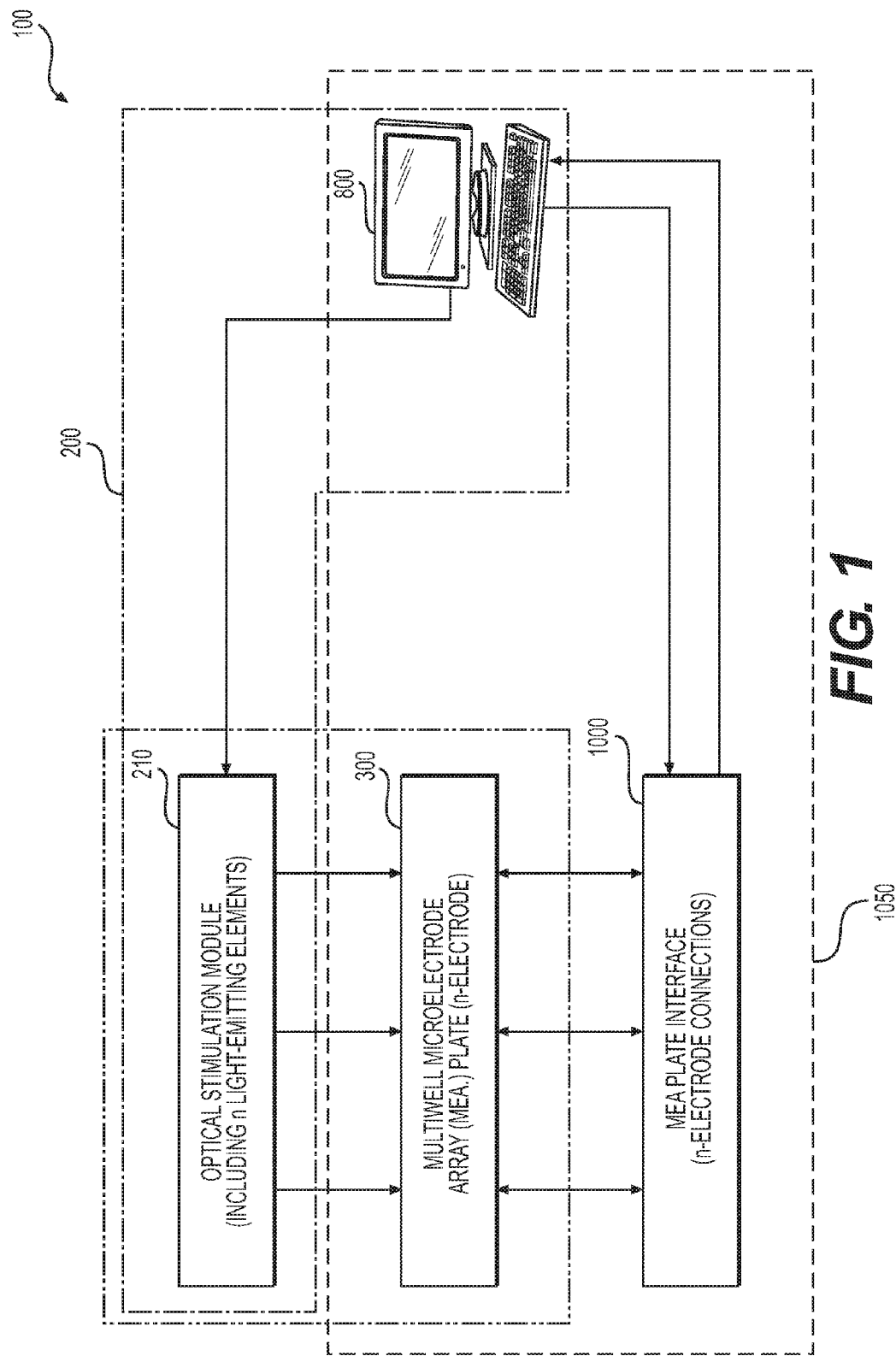
FIG. 1 illustrates an example system having a multiwell microelectrode array with optical stimulation delivery capability for controllable stimulation of culture wells, in accordance with certain disclosed embodiments.

FIG. 1 illustrates an exemplary electro-optical stimulation delivery system 100 having a multiwell microelectrode array and optical stimulation delivery capability in accordance with certain disclosed embodiments. The electro-optical stimulation delivery system 100 illustrated in FIG. 1 may provide a platform for controlling delivery of optical (and, in some cases, electrical) stimulation to a subset of culture wells and actively monitoring the electrical activity associated with the cells contained in the well. The electro-optical stimulation delivery system 100 may include, among other things, an optical stimulation module 210, a multiwell microelectrode array 300, and an MEA plate interface 1000.

Optical stimulation module 210 is also referred to herein as "optical stimulation device." In some embodiments, an optical stimulation module may be integrated with the MEA plate. In other example embodiments, an optical stimulation module may be a standalone device that detachably couples to an MEA plate. For example, the optical stimulation module may couple to the top of the MEA plate or may be coupled to the bottom of the MEA plate. Other configurations are possible as well and the language herein is not intended to limit the possible implementations of the optical stimulation module.

Those skilled in the art will recognize that the components described above with respect to electro-optical stimulation delivery system 100 are exemplary only and not intended to be limiting. Consequently, electro-optical stimulation delivery system 100 may include additional, and/or different components than those shown in FIG. 1 without departing from the scope of the present disclosure. Each of the individual components of electro-optical stimulation delivery system 100 shown in the embodiment illustrated in FIG. 1 will be described in greater detail below.

Although FIG. 1 illustrates optical stimulation module 210 and multiwell MEA plate 300 as separate elements, it is contemplated that one or more of the features of optical stimulation module 210 may be included as part of multiwell MEA plate 300 (or vice versa). Indeed, certain embodiments contemplate a multiwell microelectrode array with integrated optical stimulation capabilities, regardless of whether the optical stimulation capabilities are provided by a separate, standalone system (as shown in FIG. 1), or by an integrated solution as part of a multiwell MEA plate 300.

Figure 2:
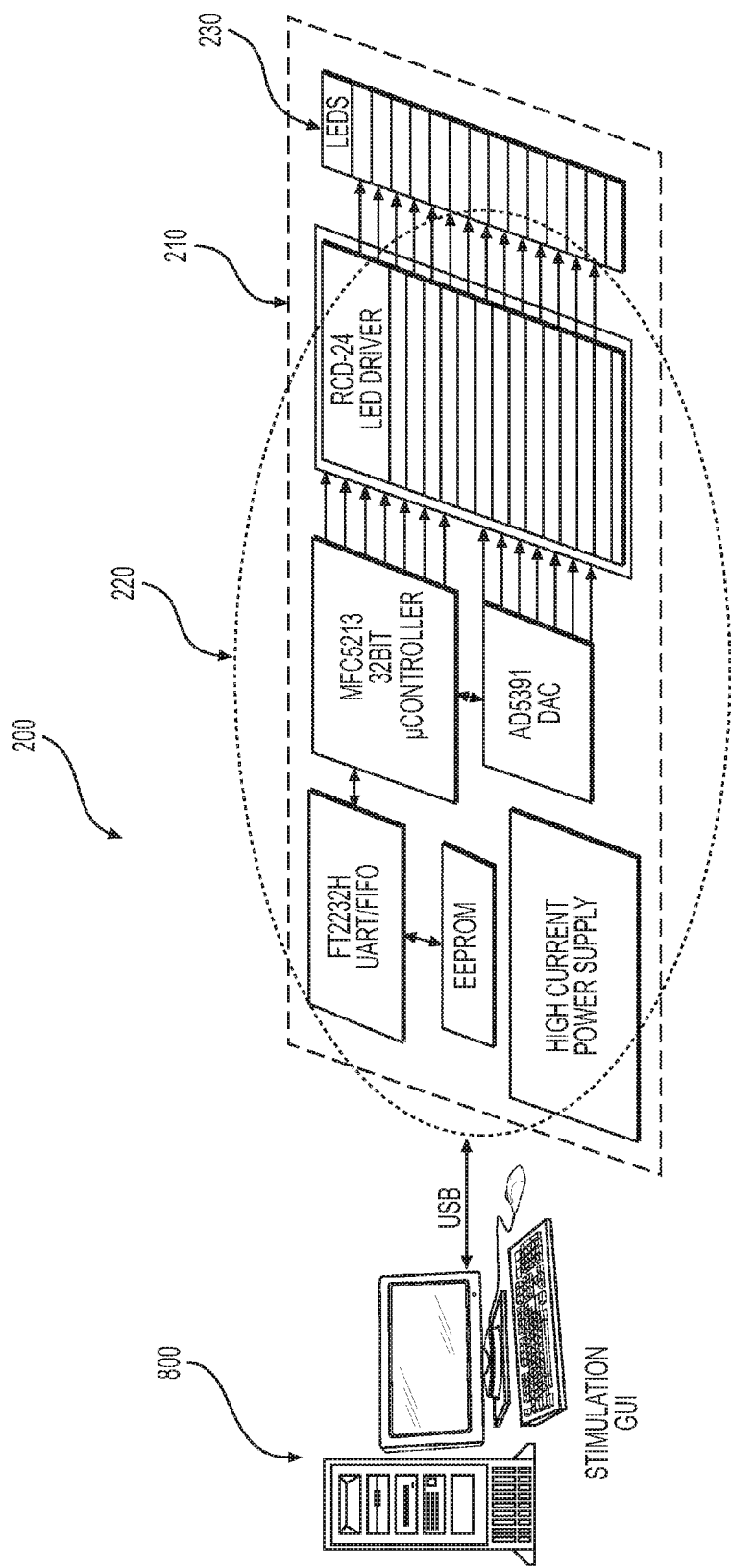
FIG. 2 provides a detail view of an optical stimulation control and delivery portion of the system illustrated in FIG. 1, consistent with certain disclosed embodiments.

FIG. 2 illustrates a schematic block diagram of an optical stimulation delivery system 200. Optical stimulation delivery system 200 includes a plurality of components that control the delivery of optical stimulation to MEA plate 300. As illustrated in FIG. 2, and in accordance with one embodiment, optical stimulation delivery system 200 may include an optical stimulation module 210 and a control and monitoring system 800 that is programmed to control optical stimulation module 210.

Optical stimulation module 210 may include one or more light-emitting element sets 230 that may be optimized/customized to meet most any power and thermal criteria that may be required. Optical stimulation module 210 may also include control circuitry 220 for independently controlling the light-emitting elements with light patterns of high temporal resolution, as well as finely graded control over output intensity. The system may also include interactive software that will enable generation of customizable stimulation waveforms, and visualization of these delivered stimulation waveforms. As such, the presently disclosed system may be configured to manage cell-targeted activation or inhibition for multiple cultures in a multiwell MEA. The term "light-emitting element set" is not intended to limit the number of light-emitting elements within a given "set." For example, a light-emitting element set may comprise one, or multiple, light-emitting elements.

Figure 4:
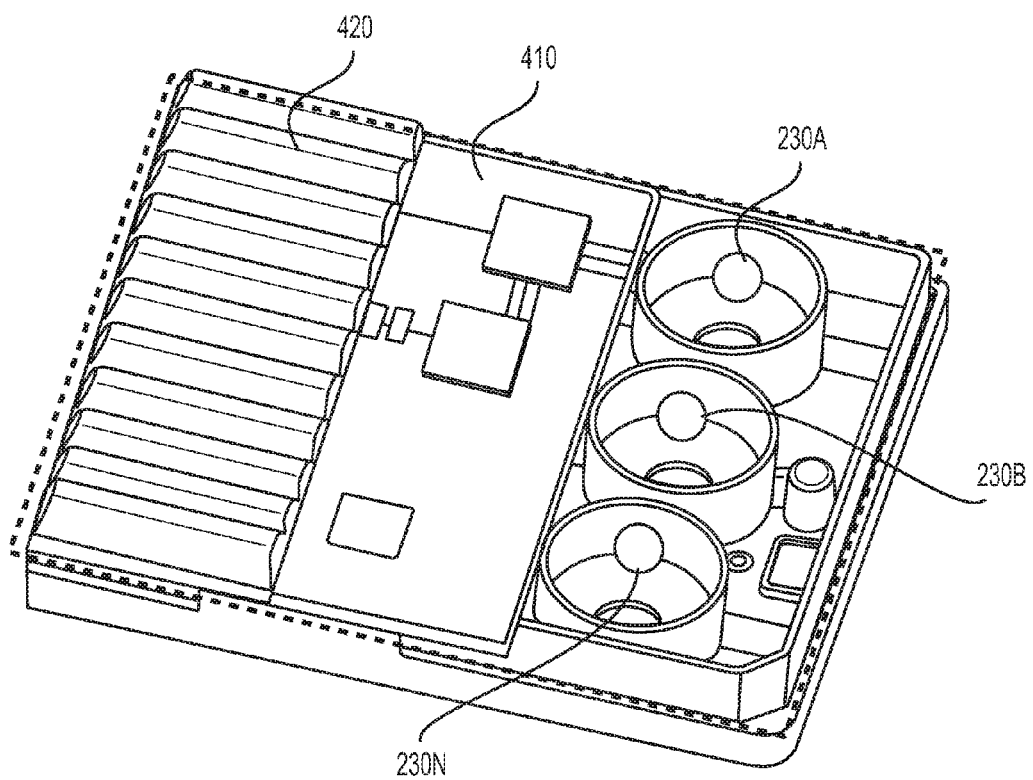
FIG. 4 provides a diagrammatic perspective view of a multiwell microelectrode array (MEA) with a detachable optical stimulation module coupled to the MEA, consistent with certain disclosed embodiments.

As shown in FIG. 2, each of light-emitting element sets 230 may include or embody any suitable component for delivering optical energy to a respective culture well with which the light-emitting element is associated. According to one embodiment, (and as illustrated in FIG. 4), light emitting diodes (LEDs) may be provided in an overlying or lid-based array (at least one LED per well). This configuration is particularly advantageous in situations where a compact, topside form factor may be required. Importantly, however, although certain embodiments call for a single LED per well, it is certainly contemplated that light-emitting element sets may include multiple light-emitting elements per well (as illustrated, for example, in FIG. 6). It is contemplated that, although LEDs are described in certain exemplary embodiments as the light-emitting elements, any of a number of light-emitting sources may be adapted for implementation. For example, light-emitting elements may include or embody any (or a combination) of lasers, organic light-emitting diodes (OLEDs), 2D pixel displays, digital light projection (DLP) technology, a waveguide element, a light-emitting carbon nanotube, or any other element suitable for providing a controllable light source for delivering optical energy to the culture well.

As illustrated in FIG. 2, each light-emitting element 230 may be coupled to control and monitoring system 800 via control circuitry 220. Light-emitting elements 230 may be controlled by any of a number of commercially available control modules. In embodiments that implement LEDs as the light-emitting elements, current-control modules (e.g., RCD24-1.0, RECOM) may be used. Such circuits may be used to control high intensity LEDs (e.g., Oslon SSL, Osram Opto Semiconductors) of one or more wavelengths. Light-emitting elements 230 may be configured to deliver one or more of infrared light energy, ultraviolet light energy, or visible light energy, depending upon the type of experiment being performed (and/or the type of light-reactive opsin being targeted, in the case of optogenetics applications).

Control circuitry 220 for the optical stimulation device may be configured to independently control individual light-emitting elements or may control sets of multiple light-emitting elements as a group. System control may be handled by a 32-bit microcontroller (e.g., MCF 5213; Freescale). Each LED in the array might be driven by an RCD24-1.0 LED Driver. This driver may control LED intensity with an analog input signal, which may be set by the microcontroller through a high channel count digital to analog converter (AD5391, Analog Devices). The driver may also take a digital on/off signal for pulsed or triggered waveforms. The microcontroller may be programmed via a high speed USB-to-UART/FIFO (FT2232H, FTDI) chip.

According to an exemplary embodiment, light-emitting elements 230 may be positioned above individual wells on an n-well MEA plate and driven continuously or modulated at a fixed or variable current during electrical recordings. The presently disclosed multiwell microelectrode array with coupled optical stimulation module may be configured to reduce both steady-state and transient noise caused by the light-emitting elements. Steady-state electrical noise may be eliminated with proper grounding of the LED driver circuitry. Electrically-induced transient noise may be reduced/eliminated by placing a transparent, electrically conductive, grounded layer (e.g., indium tin oxide (ITO)) between the LED and MEA well. When present, any photoelectric artifact may be reduced with, for example, typical bandpass filtering used for recordings of electroactive cells (e.g. 200-3000 Hz bandpass filter for spike signals (e.g., neural or cardiac)).

Figure 3A:
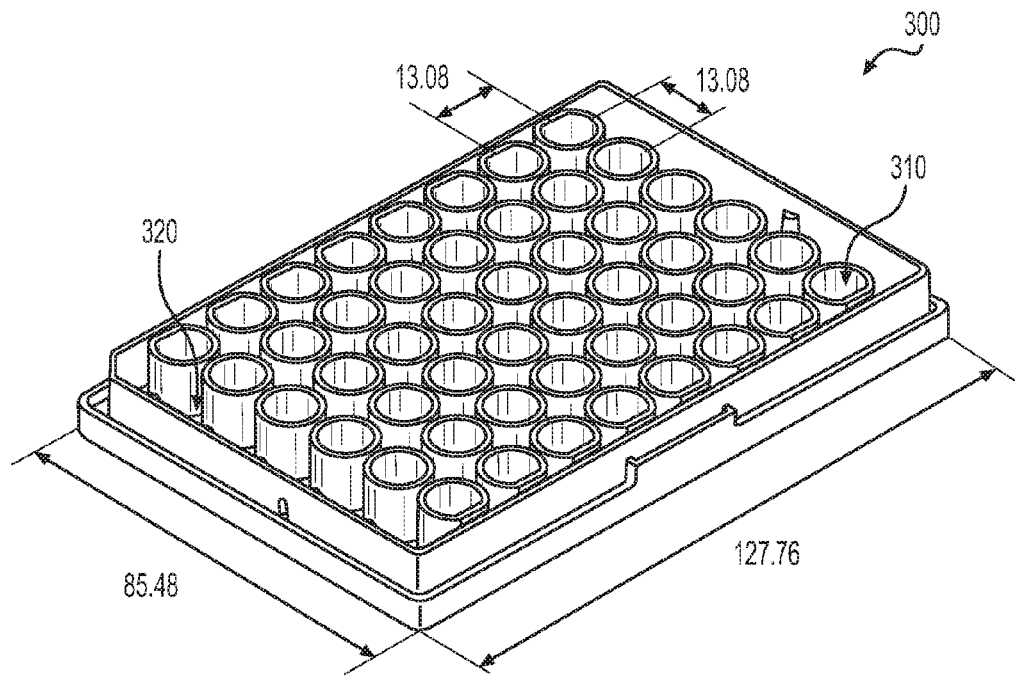
FIG. 3A provides a diagrammatic perspective view of an example 48-well microelectrode array (MEA), consistent with certain disclosed embodiments.
Figure 3B:
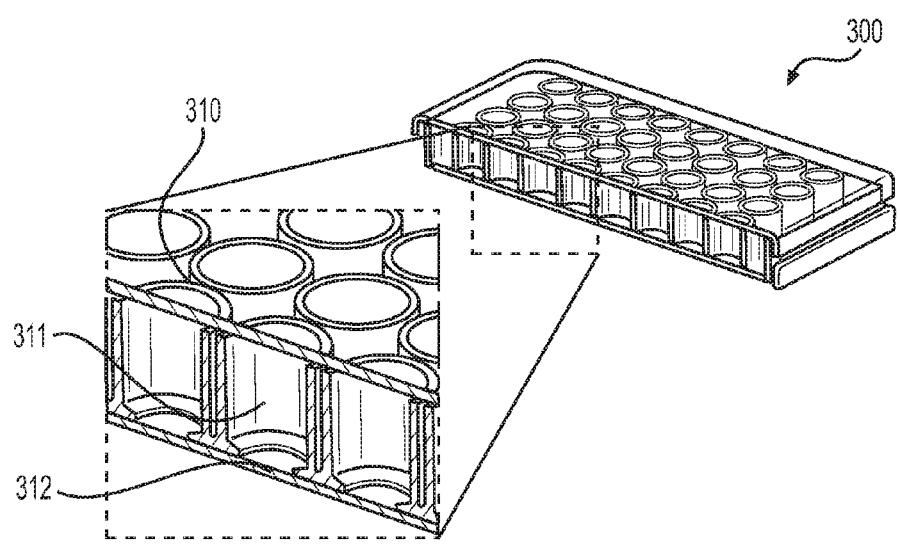
FIG. 3B provides a zoomed diagrammatic perspective view of a selection of wells of a 48-well microelectrode array (MEA), in accordance with certain disclosed embodiments.

As explained, electro-optical stimulation delivery system 100 comprises one or more components that cooperate to deliver optical (and, in some embodiments, electrical) stimulation to one or more of a plurality of culture wells in a multiwell microelectrode array device 300 and simultaneously detect electrical signals from the culture wells, including those signals that are indicative of the cellular response to the stimulation FIGS. 3A and 3B each provide a diagrammatic perspective view of the structural components of a multiwell culture array 300. As illustrated in FIGS. 3A and 3B, a multiwell culture device (regardless of whether it is configured as a multiwell MEA or multiwell MEA with optical stimulation capabilities) typically includes a plurality of culture wells 310 disposed upon substrate 312. FIG. 3A illustrates multiwell array 300 as a 48-well device. It is contemplated, however, that any number of wells may be provided without departing from the scope of the present disclosure. Furthermore, the dimensions shown in FIG. 3A are exemplary only, and not intended to be limiting. According to an exemplary embodiment, the presently disclosed multiwell arrays may be sized and configured in an ANSI-SLAS compliant format, compatible with traditional plate readers and automated instrumentation.

Multiwell MEA 300 includes a matching lid designed for maintaining sterility and reducing media evaporation. Each culture well comprises an internal volume for receiving cell culture material at an opening in the top of the well. In one embodiment, cells can be added within a small drop to the center of the well (where the MEA electrodes reside). After the cells have an opportunity to attach to the substrate, then the well can be flooded with more cell culture medium. Electrical signals resulting from cellular reactions can be monitored by electrodes positioned in the bottom of culture well. Electrical connections for connecting the electrodes to MEA plate interface 1000 are located on the bottom-side of the device. It is contemplated that the multiwell MEA might be used along with other biological, environmental, or chemical samples aside from cell cultures.

As shown in FIG. 3B, each culture well 310 may embody a receptacle for receiving cell culture and/or tissue material through an opening at the top of the well. According to one embodiment, the walls 311 and/or substrate and/or lid of culture well 310 may be comprised of or coated with reflective material to maximize the light delivery to the base of the well and to prevent light absorption or loss through the wall of the well. According to one embodiment, reflective white-walled multiwell plates may be used to increase light delivery by reflecting and concentrating light within the wells, while blocking passage of light to adjacent wells. Additionally, light delivery may be increased through the use of commercially available clear media, as culture media dyed with Phenol Red was found to significantly absorb blue and green light. Electrodes (not shown) positioned at the base 312 of the culture well 310 can be configured to provide electrical stimulation and monitor any electrical cellular, biological, or chemical activity or cellular, biological, or chemical sample properties within a given well.

Figure 5:
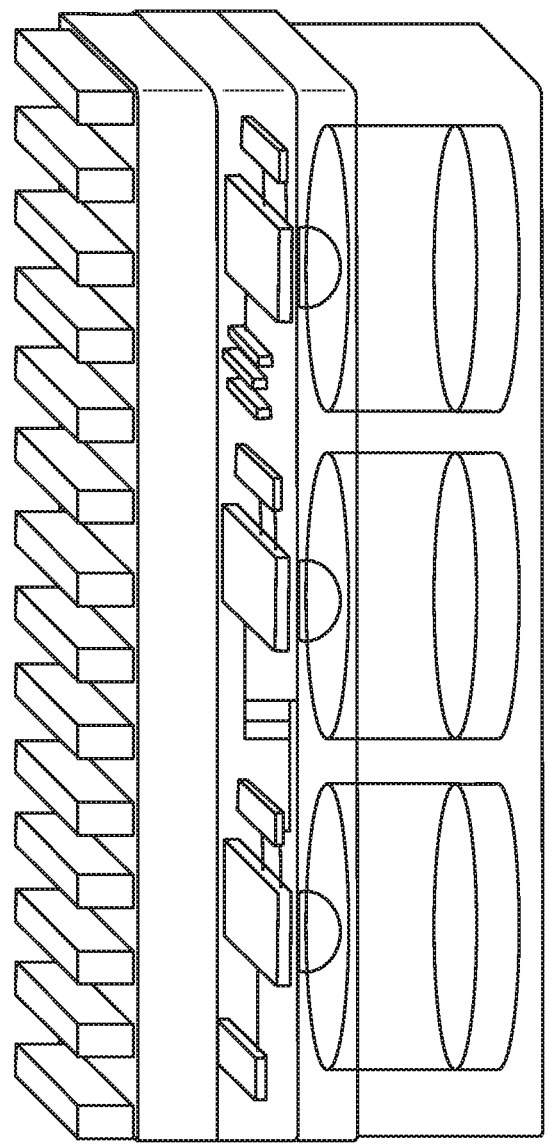
FIG. 5 provides a schematic block diagram of a cross-section of a multiwell microelectrode array (MEA) with a detachable optical stimulation module coupled to the MEA, in accordance with certain disclosed embodiments.

FIGS. 4, 5, and 6 illustrate an exemplary configuration of the multiwell microelectrode array 300 with coupled optical stimulation module 210 consistent with the disclosed embodiments. Typical mid- to high-power LEDs can draw high current loads and dissipate significant heat. For example, a high power 465 nm blue LED might consume 1 W power and dissipate 0.5 W of heat when run at a moderate supply current of 350 mA. These types of power and thermal costs scale with LED count, required light intensity, and stimulation duty cycle. Consequently, the presently disclosed system includes robust power supply circuitry 410 with dedicated control of the current delivered to each LED (230A, 230B, 230N). As shown in FIGS. 4 and 5, multiwell MEA 300 may include one or more components for managing heat dissipation to ensure efficient LED operation, prevent LED device damage, and reduce the amount of heat delivered to cell cultures. The system may utilize metal core printed circuit boards and, in some embodiments, a custom aluminum or copper heat sink 420 with an optional active cooling system. Although FIGS. 4 and 5 illustrate the optical stimulation module 210 having a single LED per set, it is contemplated that each set may include a plurality of independently controllable light emitting elements 650 configured to deliver multiple wavelengths of light to each well.

FIG. 6 illustrates an exemplary multiwell microelectrode array with a coupled optical stimulation module, where each light-emitting element set includes a plurality of light-emitting components 650. Each light-emitting component may be configured to deliver a different wavelength and/or intensity of light to provide greater flexibility in the types of experiments that can be performed. In addition to multiple light-emitting elements, the multiwell MEA 300 may also include one or more devices for enhancing the delivery of optical energy to the culture well. For example, as illustrated in FIG. 6, multiwell MEA 300 may include one or more light-collimating reflectors 640 for directing the optical energy to the center of the culture well. Alternatively or additionally, multiwell MEA 300 may also include other components, such as lenses, filters, gratings, and other components for modifying the optical properties depending upon the specific needs of the experiment. These features might be incorporated into the lid 610 of the multiwell plate. For example, lenses and recesses can be inexpensively molded into a low-cost disposable multiwell plate lid.

As also illustrated in FIG. 6, the optical stimulation module 210 may be configured to overlay a transparent lid 610 associated with the multiwell MEA 300. This configuration may allow the optical stimulation module 210 to be coupled and de-coupled from multiwell MEA 300, without potentially contaminating the cultures during testing. In this configuration, optical stimulation module 210 may be designed to removably couple to/from lid 610. As an alternative to the optical stimulation module 210 being removably coupled to a separate lid, it is contemplated that optical stimulation module 210 may be integrated with lid 610, or constructed to be the lid for the multiwell MEA 300.

Although FIG. 6 illustrates light-emitting elements that are configured for positioning at the opening of (i.e., above) multiwell MEA 300, it is contemplated that the light-emitting elements may be embedded in a circuit board beneath a transparent floor of the respective wells. According to one exemplary embodiment, light emitting elements may be provided beneath or within substrate 620 upon which the grid of electrodes is disposed. In this embodiment, the electrodes may be printed on a transparent substrate (e.g., Printed Circuit Board (PCB), flex circuit, or transparent biosensor array) through which light can pass. According to other embodiments, light emitting elements may be included as part of the same transparent substrates upon which electrodes are disposed. Organic Light Emitting Diode (OLED) technology can be coupled with micro-biosensor fabrication technologies to achieve such an integrated transparent OLED-MEA substrate.

According to additional and/or different embodiments, the multiwell MEA 300 may also include enhancements to facilitate efficient conservation/delivery of light emitted by optical stimulation module 210. For example, multiwell MEA 300 may include strategically shaped or curved walls 660 to ensure more concentrated light delivery toward the central portion of the bottom of the well. Alternatively or additionally, multiwell MEA may include a reflective material 630, disposed beneath each well and configured to reflect light that is transmitted through the bottom of the well back into the well (in the case of a transparent substrate 620). The MEA lid 610 may also incorporate modifications to increase, enhance, shape, or otherwise influence light delivery to the MEA culture. For example, lenses might be molded into the lid to collimate or refract light to the center of the well. A Fresnel lens design might accomplish this while extending minimally into the well. The light might have recesses to allow light sources such as LEDs or optical fibers to extend some depth into the well, increasing light delivery, or directing light to one or more particular regions of the culture. To minimize condensation that might collect on the lid in the course of typical use, possibly interfering with light delivery, a system of heating the lid might be employed. In one example, a transparent ITO layer, might be used to heat the lid and minimize condensation. In the case of bottom-side light delivery, the lid might be reflective, to re-direct and concentrate light back into the culture well.

As explained, multiwell MEA 300 includes one or more electrodes, each of which is configured to measure electrical activity in the surrounding area. Multiwell MEA 300 includes one or more electrode sets, each electrode set comprising one or more (e.g., 8) electrodes, with each set disposed between the substrate 312 and the base of a respective culture well that it is configured to monitor. The term "electrode set" is not meant to limit the number of electrodes in the "set." For example, an electrode set may comprise a single electrode or multiple electrodes.

Figure 7A:
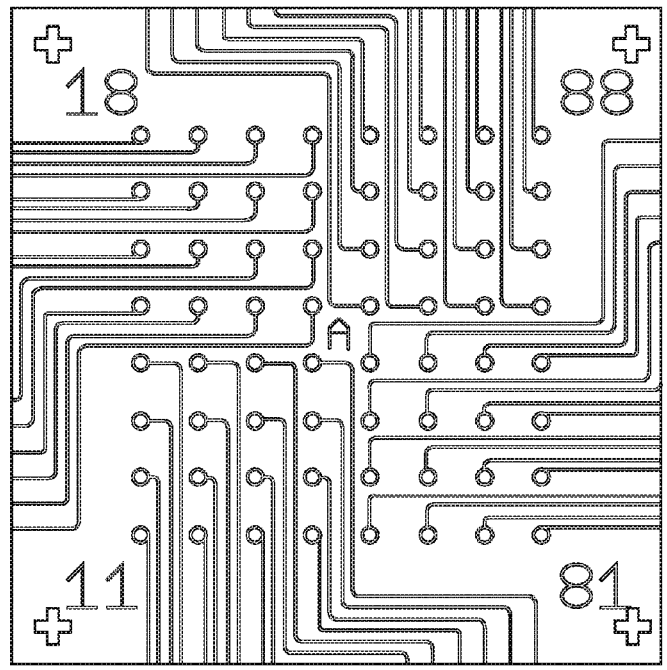
FIG. 7A provides an overhead (top) view of an exemplary single well (i.e., corresponding to a single culture well of a multiwell MEA) 8×8 grid of electrodes used in the presently disclosed multiwell microelectrode array (MEA) with optical stimulation capabilities, in accordance with certain disclosed embodiments.

FIG. 7A illustrates a schematic of an exemplary electrode array. As shown in FIG. 7A, electrode arrays are made up of a grid of tightly spaced electrodes, and each electrode is capable of simultaneously monitoring the activity of individual cells. As illustrated in FIG. 7A, the arrangement of multiple electrodes in a grid extends the recording range across a relatively large area, providing concurrent access to both single cell and tissue- or network-level activity. The control and monitoring of this cellular activity is made possible by the electronics, which impart multiple functions to each electrode.

Each electrode of the array facilitates monitoring of single-cell and network-level activity for extended periods of time, with virtually no destructive interference to the tissue being investigated. In fact, the broad access to network information, along with the minimally invasive nature of the device, is precisely what makes the MEA an exceptional single-cell and network-level research tool. Each electrode in the high throughput MEA is ideally suited for investigation of electroactive cells and tissue (e.g., neural, cardiac, muscle, and spinal tissue). As explained previously, the MEA-wells are organized in an ANSI-SLAS compliant format, compatible with traditional plate readers and automated instrumentation. Within each well, a plurality (e.g., between 4 and 64 individual embedded microelectrodes (~30-50 μm diameter; ~200-350 μm center-to-center spacing, in accordance with an exemplary embodiment) with integrated ground electrodes are capable of simultaneously monitoring the activity of individual cells. The arrangement of these electrodes into a grid extends the recording range up to a 1.5×1.5 mm area, providing concurrent access to both single-cell and network-level activity.

Figure 7B:
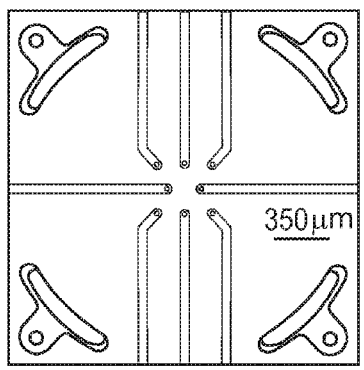
FIGS. 7B and 7C provide detail overhead (top) zoom views of an exemplary single (i.e., corresponding to a single culture well of the multiwell MEA) 8-microelectrode array used in the presently disclosed multiwell microelectrode array (MEA) with optical stimulation capabilities, consistent with certain disclosed embodiments.
Figure 7C:
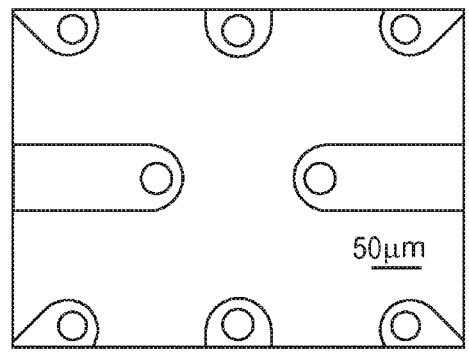

FIGS. 7B and 7C provide more detailed views (i.e., zoom) views of each electrode set associated with an embodiment of the multiwell MEA 300 consistent with the present disclosure. According to one embodiment, each electrode is constructed of nano-textured gold on an FR4 epoxy resin with an optional reflective white overlay to reflect light back into the culture well for increased irradiance of the cell cultures. Nano-texturing of gold is achieved through proprietary processes designed to increase the surface area of gold, thereby lowering the electrode impedance and noise.

Each of the electrodes in every set of one or more electrodes may be configured to simultaneously provide stimulation to the culture well and record electric signal resulting from stimulation of the cells. Alternatively or additionally, some of the electrodes in the set may be configured to provide stimulation only, while other electrodes are dedicated to recording cellular activity.

As explained, processes and methods consistent with the disclosed embodiments provide solutions for integrating optical stimulation in a multiwell MEA 300. In addition to the structural and functional aspect of the multiwell MEA 300, the present disclosure is directed to processes and methods for using the multiwell MEA 300 to perform high-throughput, large scale testing, such as testing based on optogenetics techniques. Consequently, the presently disclosed electro-optical stimulation delivery system 100 includes a computer system (or stimulation GUI) that has been customized to control the stimulation of the culture wells and provide an interface for collecting/analyzing the cellular activity resulting from the stimulation.

FIG. 8 illustrates an exemplary schematic diagram associated with the control and monitoring system 800 that is adapted to interface with a multiwell microelectrode array (MEA) with optical stimulation capabilities. As explained, control and monitoring system 800 may include processor-based device that includes its own microcontroller, volatile and non-volatile memory, one or more databases, and one or more interfaces for communicating data with a user.

According to one embodiment, control and monitoring system 800 may include one or more hardware components including, for example, a central processing unit (CPU) or microprocessor 811, a random access memory (RAM) module 812, a read-only memory (ROM) module 813, a memory or data storage module 814, a database 815, one or more input/output (I/O) devices 816, and an interface 817. Alternatively and/or additionally, control and monitoring system 800 may include one or more software media components such as, for example, a computer-readable medium including computer-executable instructions for performing methods consistent with certain disclosed embodiments. It is contemplated that one or more of the hardware components listed above may be implemented using software. For example, storage 814 may include a software partition associated with one or more other hardware components of control and monitoring system 800. Control and monitoring system 800 may include additional, fewer, and/or different components than those listed above. It is understood that the components listed above are exemplary only and not intended to be limiting.

CPU 811 may include one or more processors, each configured to execute instructions and process data to perform one or more functions associated with control and monitoring system 800. As illustrated in FIG. 8, CPU 811 may be communicatively coupled to RAM 812, ROM 813, storage 814, database 815, I/O devices 816, and interface 817. CPU 811 may be configured to execute sequences of computer program instructions to perform various processes, which will be described in detail below. The computer program instructions may be loaded into RANI 812 for execution by CPU 811.

RAM 812 and ROM 813 may each include one or more devices for storing information associated with an operation of control and monitoring system 800 and/or CPU 811. For example, ROM 813 may include a memory device configured to access and store information associated with control and monitoring system 800, including, for example, stimulation schemes for different types of experiments. RAM 812 may include a memory device for storing data associated with one or more operations of CPU 811. For example, ROM 303 may load instructions into RAM 302 for execution by CPU 811.

Storage 814 may include any type of mass storage device configured to store information that CPU 811 may need to perform processes consistent with the disclosed embodiments. For example, storage 814 may include one or more magnetic and/or optical disk devices, such as hard drives, CD-ROMs, DVD-ROMs, or any other type of mass media device. Alternatively or additionally, storage 814 may include flash memory mass media storage or other semiconductor-based storage medium. Database 815 may include one or more software and/or hardware components that cooperate to store, organize, sort, filter, and/or arrange data used by control and monitoring system 800 and/or CPU 811.

I/O devices 816 may include one or more components configured to communicate information with a component or user associated with control and monitoring system 800. For example, I/O devices 816 may include a console with an integrated keyboard and mouse to allow a user to input parameters associated with control and monitoring system 800. I/O devices 816 may also include a display including a graphical user interface (GUI) for providing a network management console for network administrators to configure control and monitoring system 800. I/O devices 816 may also include peripheral devices such as, for example, a printer for printing information associated with control and monitoring system 800, a user-accessible disk drive (e.g., a USB port, a floppy, CD-ROM, or DVD-ROM drive, etc.) to allow a user to input data stored on a portable media device, a microphone, a speaker system, or any other suitable type of interface device. I/O devices may be configured to output network analysis results and traffic characteristics.

Interface 817 may include one or more components configured to transmit and receive data via a communication network, such as the Internet, a local area network, a workstation peer-to-peer network, a direct link network, a wireless network, or any other suitable communication platform. For example, interface 817 may include one or more modulators, demodulators, multiplexers, demultiplexers, network communication devices, wireless devices, antennas, modems, and any other type of device configured to enable data communication via a communication network. According to one embodiment, interface 817 may be coupled to or include wireless communication devices, such as a module or modules configured to transmit information wirelessly using Wi-Fi or Bluetooth wireless protocols.

FIGS. 9A, 9B, 9C, 9D, and 9E provide exemplary user interface screens shots associated with control and monitoring system 800. According to one embodiment, the software may be Axion's Integrated Studio (AxIS) suite of software provided by Axion BioSystems of Atlanta, Ga. This software may provide an interface that allows users to create sophisticated stimulation experiments via I/O devices 816 and/or interface 817. This software allows concurrent monitoring of channel recordings, digital and analog filter adjustments, electrode assignment, and stimulus waveform design, all within the same application in a modular layout.

Figure 9A:
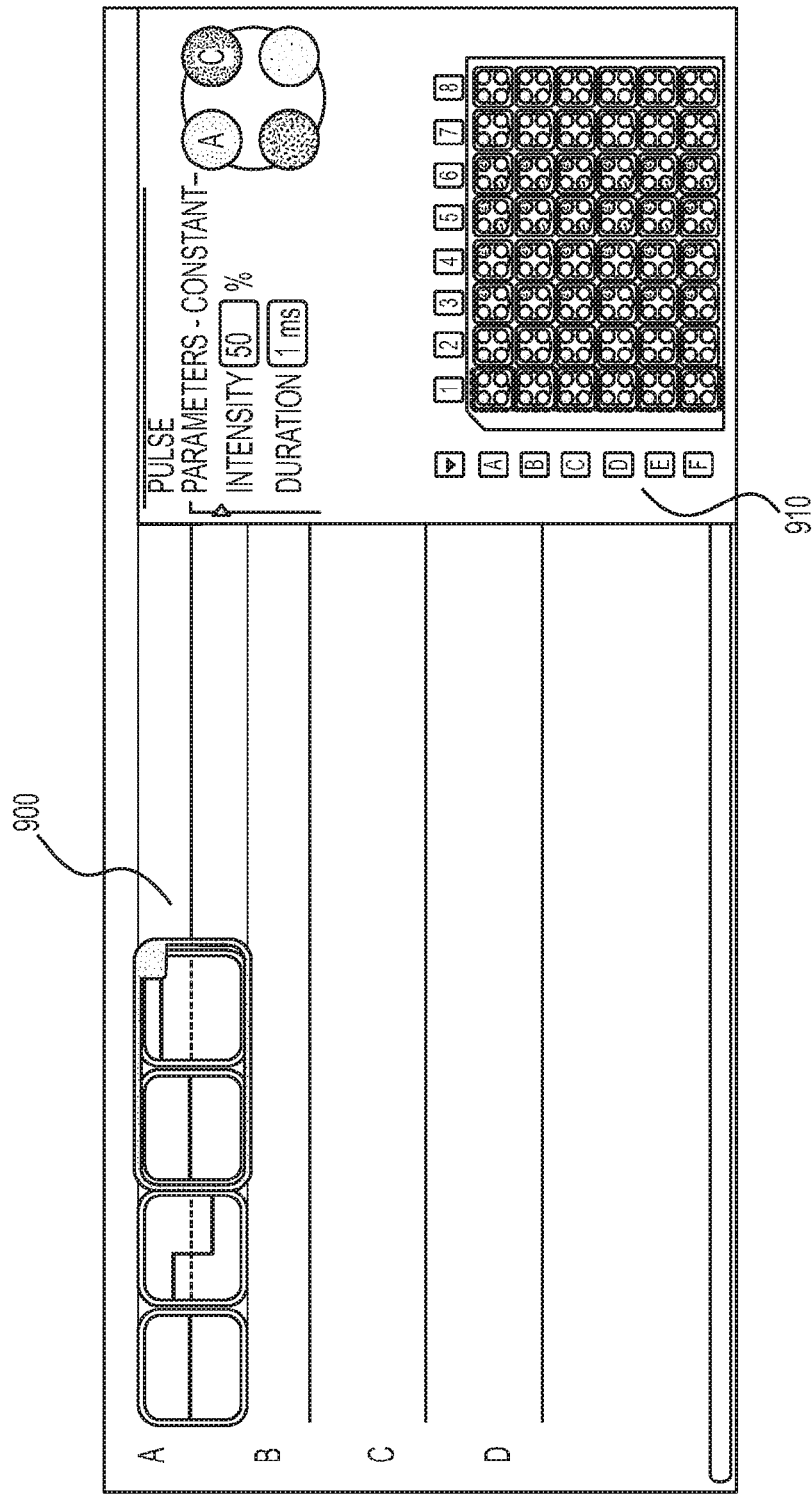
FIGS. 9A, 9B, 9C, 9D, and 9E provide screen shots associated with an example user interface associated with the integrated data analysis and control suite that is used to conduct and visualize various experiments that may be performed using the presently disclosed multiwell microelectrode array (MEA) with optical stimulation capabilities, consistent with certain disclosed embodiments.

Software associated with stimulation GUI provides an interface that allows users to control the stimulation parameters associated with the electrodes and light-emitting elements. FIG. 9A illustrates an exemplary software interface for independently controlling the stimulation parameters for each culture well. The software interface may also allow the user to establish and control stimulation parameters 900 associated with different groups of target culture wells 910. According to one embodiment, the user can control the current level and waveform type associated with electrical stimulation. Alternatively or additionally, the software interface may allow a user to control the optical stimulation parameters, such as frequency and amplitude of optical radiation.

Figure 9B:
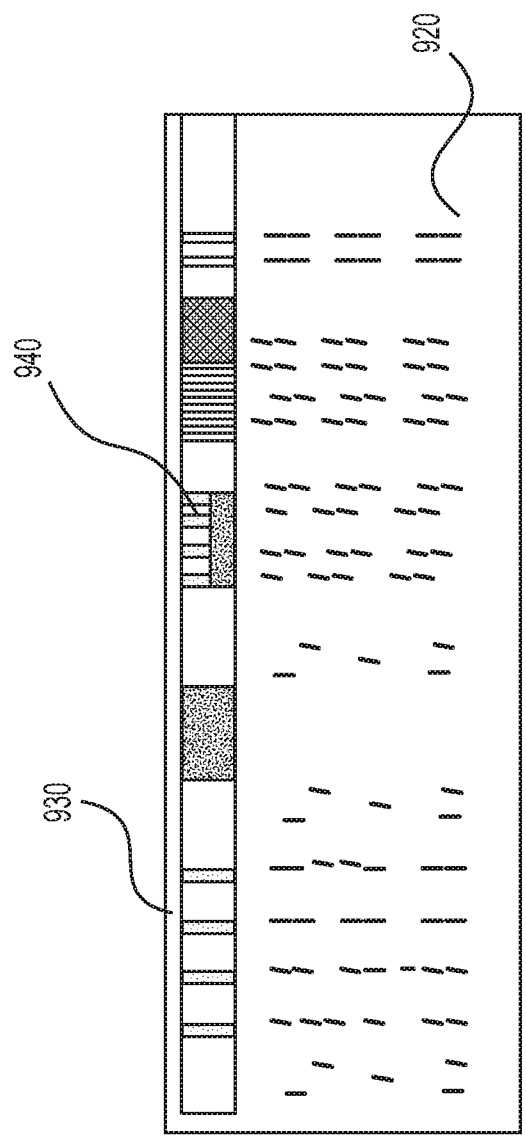

Software associated with stimulation GUI may provide an interface for monitoring real-time experiment data. FIG. 9B illustrates a screen shot of a software recording module that displays a real-time, or post-experiment, scrolling "raster" plot display of action potentials detected by each electrode in a sample MEA well. The timing of each detected action potential signal is demarcated by a vertical line 920 for each electrode in a sample MEA well. A depiction of delivered optical stimulation patterns of one 930 or more wavelengths 940 is shown on the same display. This conceptual example illustrates one way that delivered light stimulation might be visualized, and furthermore visualized in a way that is temporally aligned with electrical recordings and/or electrical stimulation from the MEA electrodes.

Figure 9C:
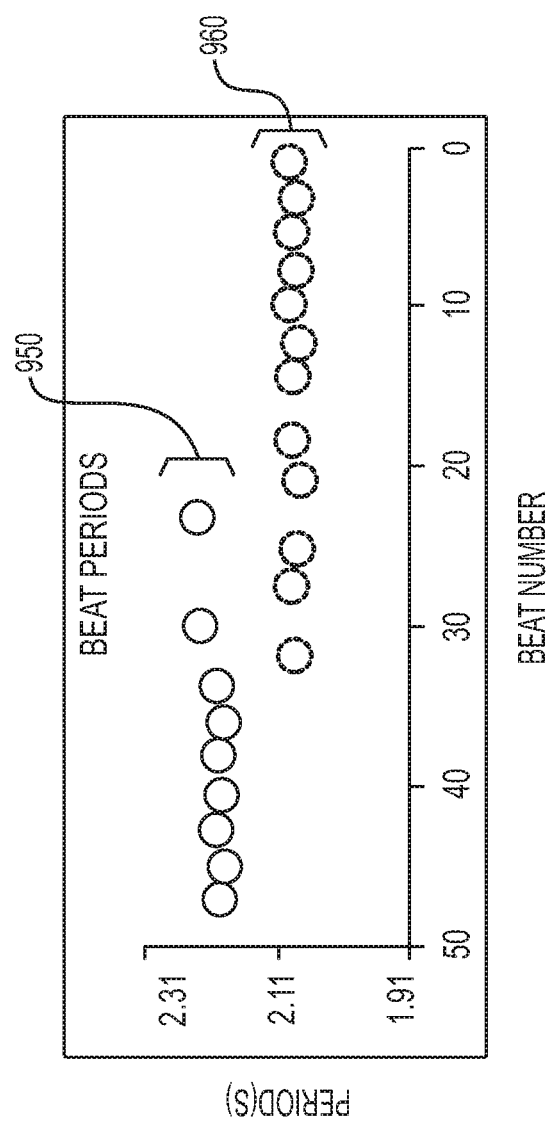

FIG. 9C provides an exemplary, conceptual software visualization illustrating metrics of detected signals that are further classified and visualized as light-evoked. In this example, beating from a cardiac cell culture is detected and analyzed, and the timing between consecutive beats, termed the beat period, is calculated and displayed as real-time beats 950. If the beats are classified as being evoked by delivered light, they are represented differently, as illustrated by beats 960, to allow the experimenter to visually assess the effects of optical stimulation.

Figure 9D:
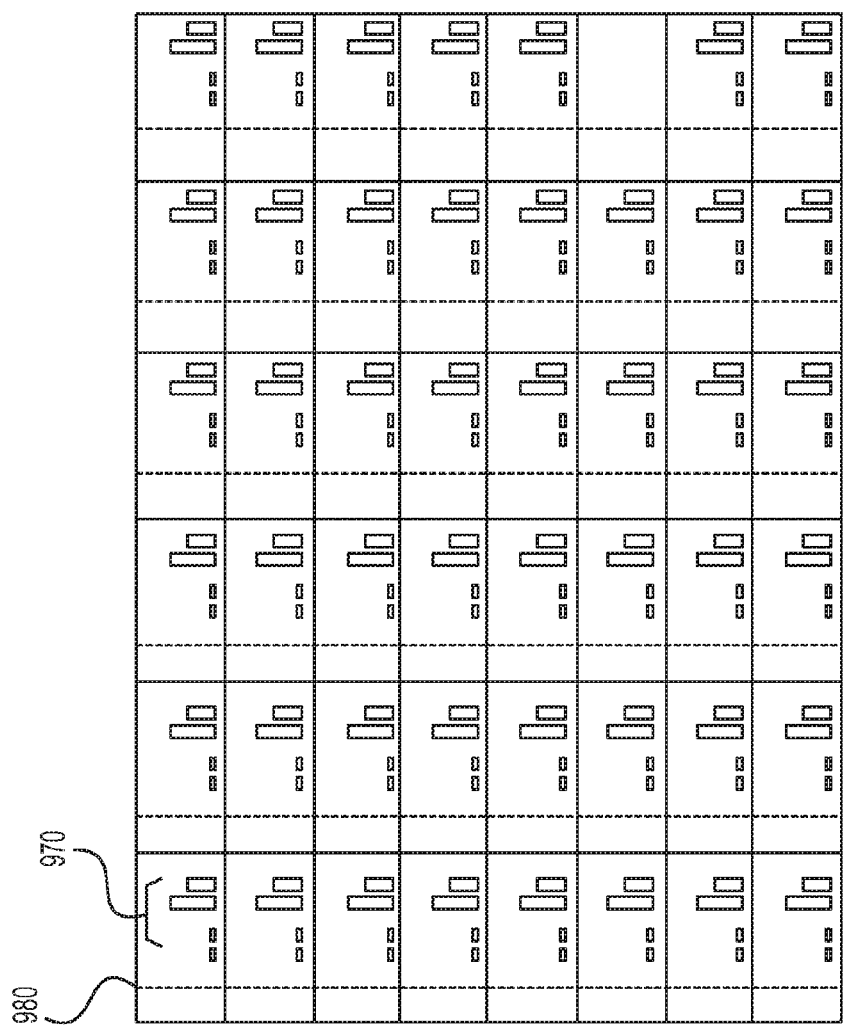

FIG. 9D provides another exemplary conceptual software visualization, whereby an activity metric is calculated and displayed in relation to delivered optical stimulation. In this example, a peristimulus time histogram of detected action potentials in relation to delivered pulses of light is generated and continually updated. Indication 980 indicates the timing of light delivery and the histogram 970 includes action potential counts falling within bins of elapsed time after each delivered light pulse.

Figure 9E:
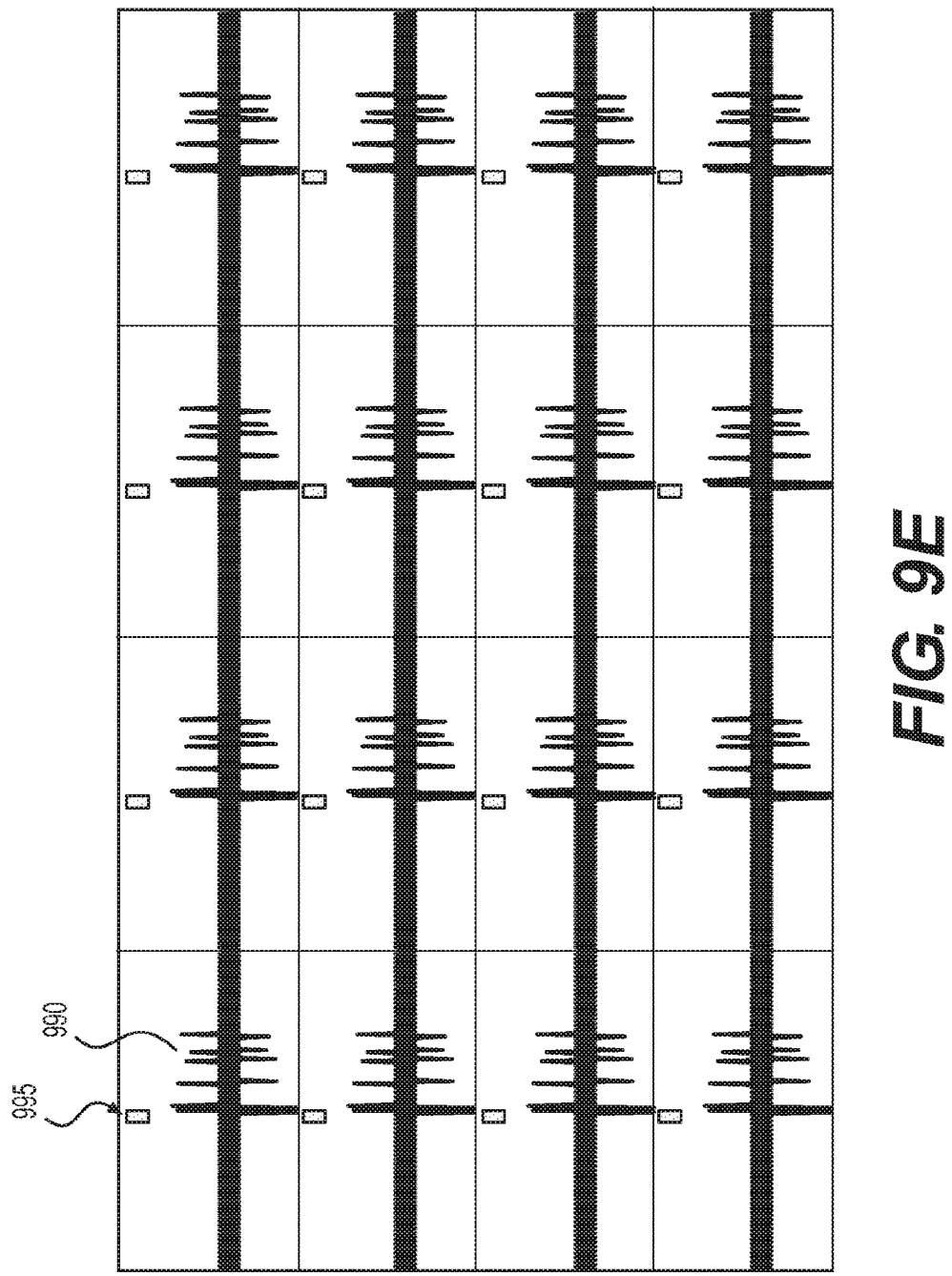

FIG. 9E provides another exemplary conceptual software visualization, whereby electrical activity 990 detected by each recording electrode is displayed in real-time or after an experiment. Characteristics of delivered light patterns, including the timing, intensity, or wavelength 995, is/are indicated graphically and superimposed on the plots of detected activity. The optical stimulation patterns are displayed in a manner that is time synchronized with the visualization of detected electrical activity. Such representations allow the experimenter to easily visually assess the impact of optical stimulation on detected signals.

Figure 10:
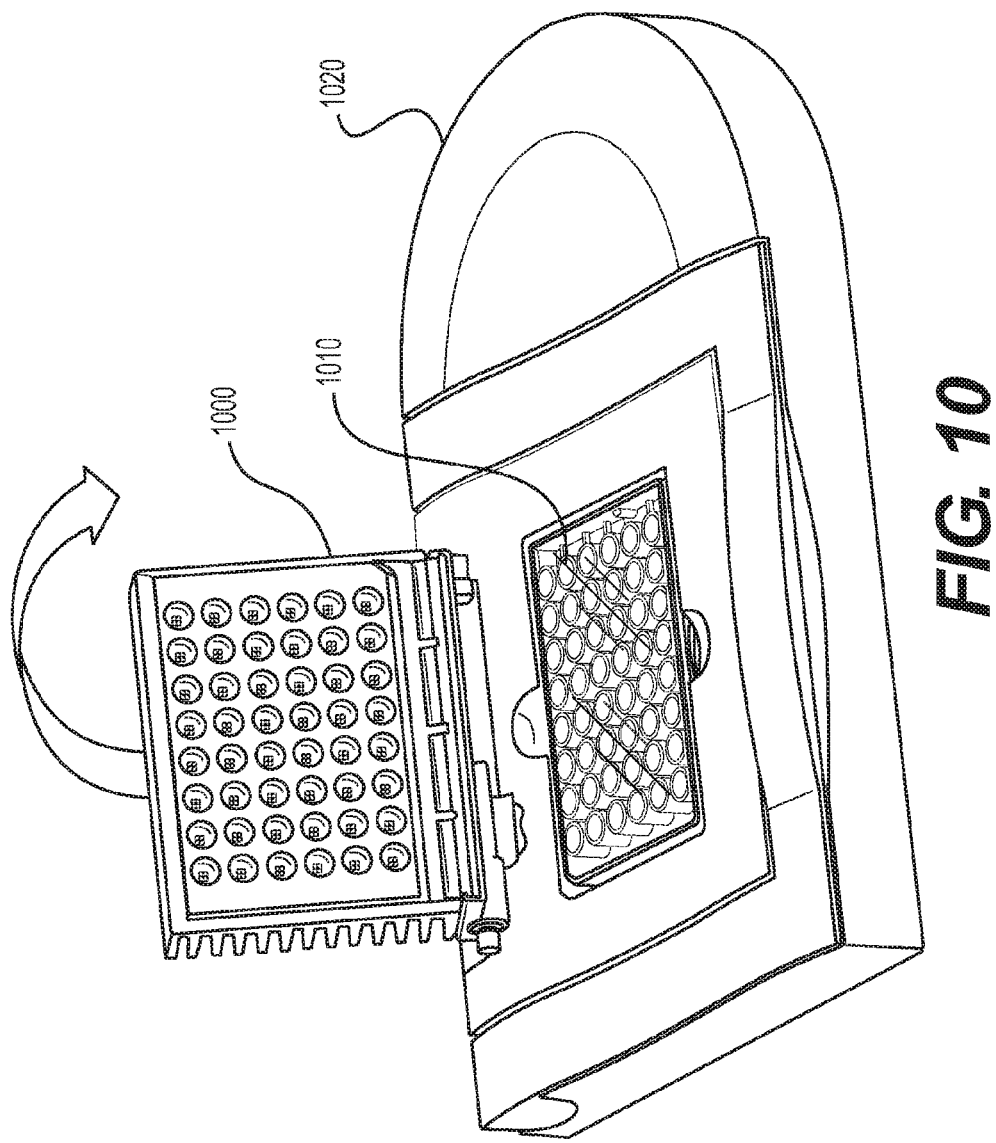
FIG. 10 illustrates an exemplary multiwell microelectrode array system containing a 48-well multiwell microelectrode array plate, and a detachable optical stimulation device for optically stimulating individual culture wells, in accordance with certain disclosed embodiments.

FIG. 10 illustrates an exemplary interface system for communicatively coupling the presently disclosed multiwell microelectrode array (MEA) with optical stimulation capabilities with a processor-based computing system having an integrated data analysis and control suite. An optical stimulation module 1000 is shown here as a detachable platform that can be placed onto the multiwell MEA plate 1010 while the plate is docked in the interface system 1020.

Figure 11:
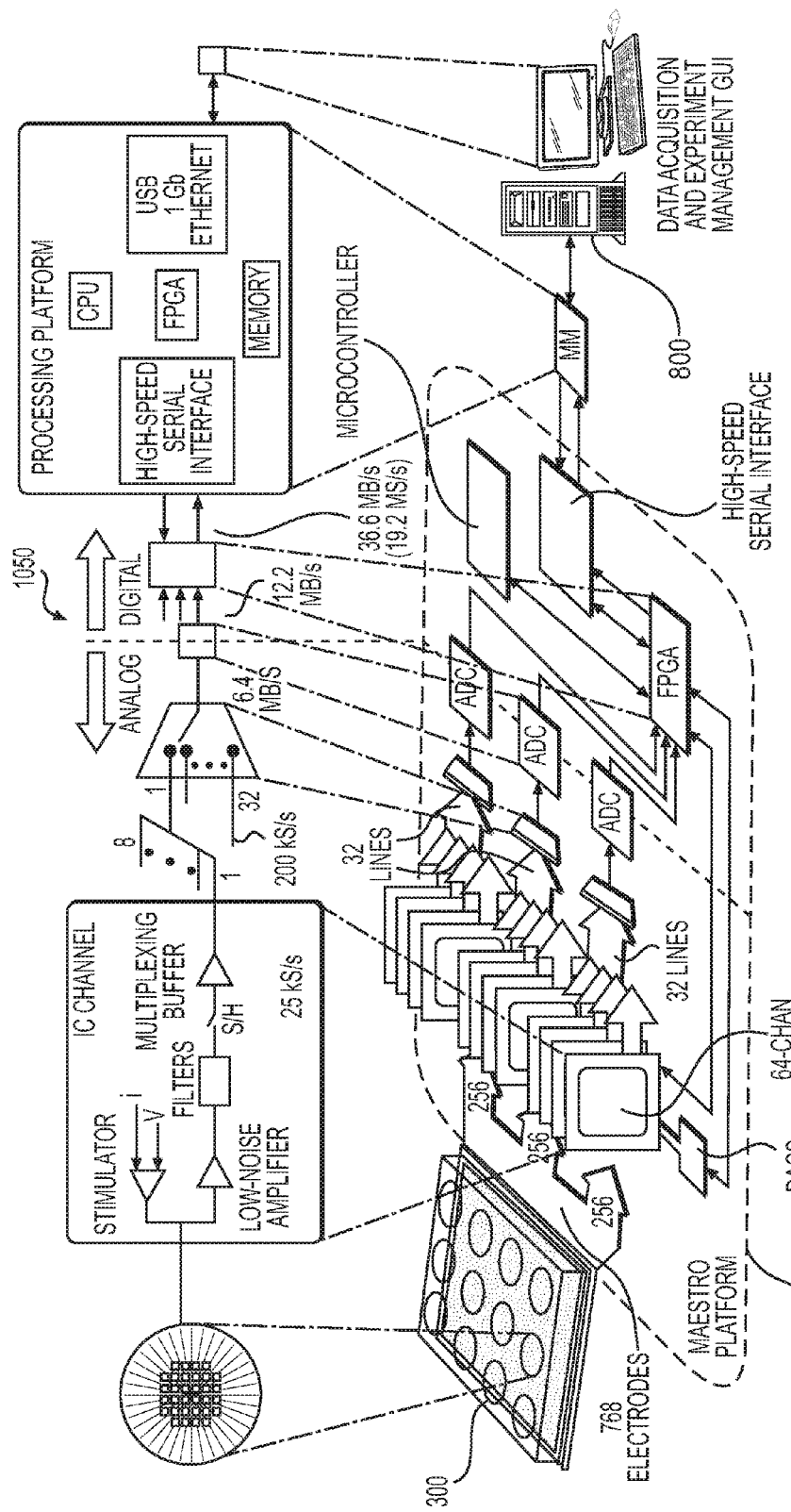
FIG. 11 provides a schematic block diagram of certain components associated with the exemplary interface system illustrated in FIG. 10 and its corresponding interactions between the multiwell MEA plate 300 and control and monitoring system 800.

FIG. 11 provides a schematic block diagram of certain components associated with the exemplary interface system illustrated in FIG. 10 and its corresponding interactions between the multiwell MEA 300 and control and monitoring system 800. Such an interface system may provide full stimulation and recording access to a plate with 768 electrodes. Three banks of 64-channel ICs interface the electrodes and multiplex the resulting signals by a factor of 8. Additional multiplexing is used to interface to a bank of ADCs, with FPGAs providing data communication, system coordination, and data processing functions.

Figure 12:
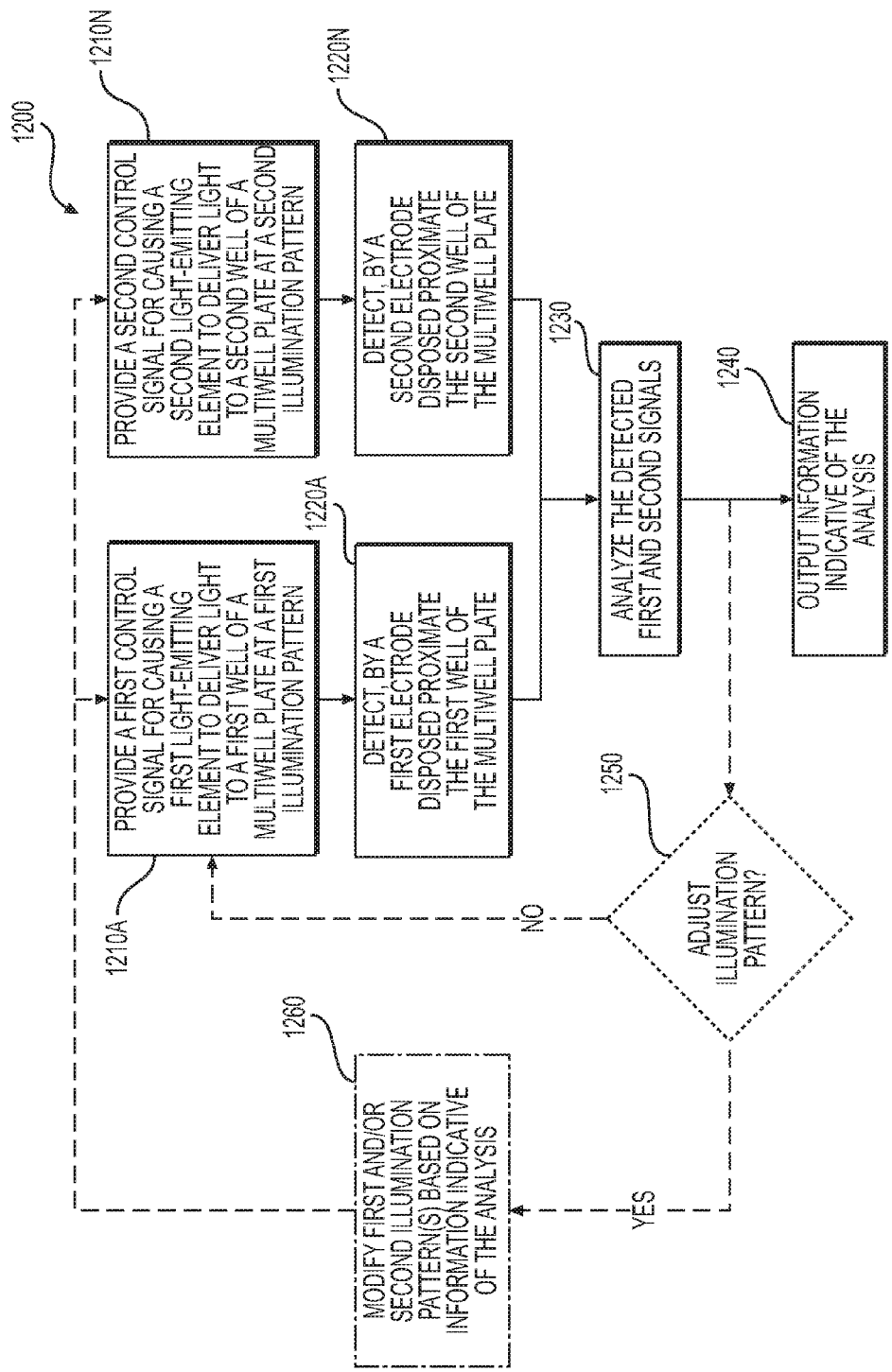
FIG. 12 provides a functional block diagram associated with an exemplary process for use and control of the presently disclosed multiwell microelectrode array (MEA) with optical stimulation capabilities, consistent with certain disclosed embodiments.

FIG. 12 provides a functional block diagram associated with an exemplary process for use and control of the presently disclosed multiwell microelectrode array (MEA) with optical stimulation capabilities. Optical patterns 1210 are delivered to one or more MEA wells. Subsequently or simultaneously, electrical signals are detected 1220 by one or more electrodes in one or more MEA wells. These detected signals are analyzed 1230 and output 1240 by the system. Optionally, the illumination pattern may be adjusted 1250, either by the experimenter or automatically by the optical stimulation module or processor, based on the analysis of detected signals 1230. For example, the intensity of delivered light pulses might be automatically adjusted on a per-well basis to an optimal level 1260, based on detected metrics of neural or cardiac cell culture activity. This feedback-driven tuning of delivered light might allow for advanced, algorithmic control over the state of cell cultures on a per well basis, allowing for advanced control and analysis of target cells and cell networks.

Figure 13:
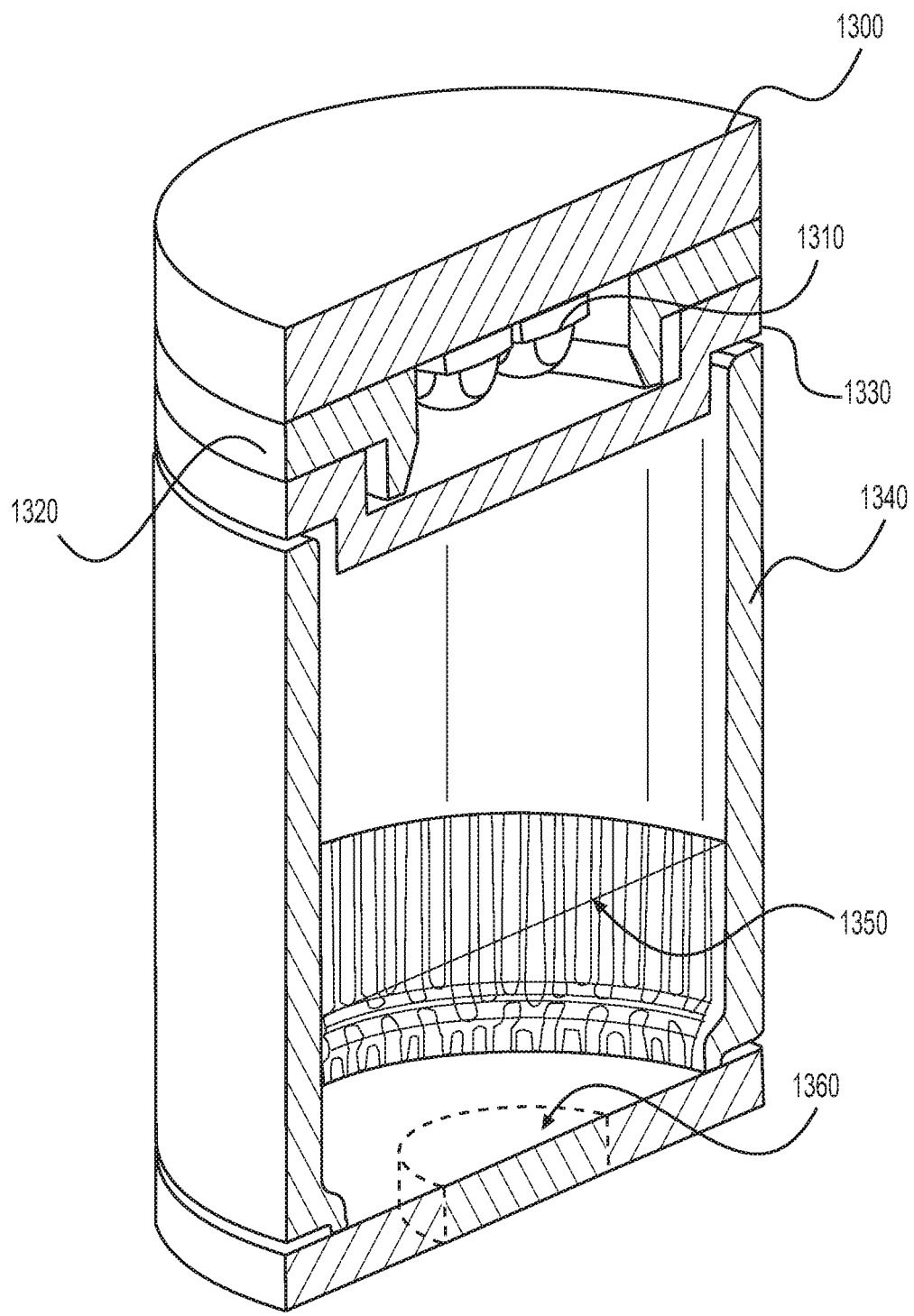
FIG. 13 provides a diagrammatic perspective view of an individual culture well within an exemplary multiwell microelectrode array (MEA) plate, along with an overlying detachable optical stimulation module, consistent with certain disclosed embodiments.

FIG. 13 provides a conceptual, perspective view of a sectioned MEA well within a multiwell MEA plate 300. In this embodiment, a transparent MEA plate lid 1330 remains on the MEA plate during use. A light delivery platform, including an array of LEDs 1310 on an electronics board 1300 substrate, and an array of reflectors 1320 or lenses fits onto the multiwell plate. Recesses in the plate lid allow for mechanical alignment, reduce the escape of light into adjacent wells, and improve the optics of light delivery. Light passes through a volume of cell culture medium 1350 which might optionally be transparent in color or colored such that the delivered light is not absorbed by the medium. Lid, reflector, and MEA plate modifications may be incorporated for the purpose of maximizing efficiency and/or providing uniform light delivery to the central target cell culture region 1360 above the grid of microelectrodes.

Figure 14A:
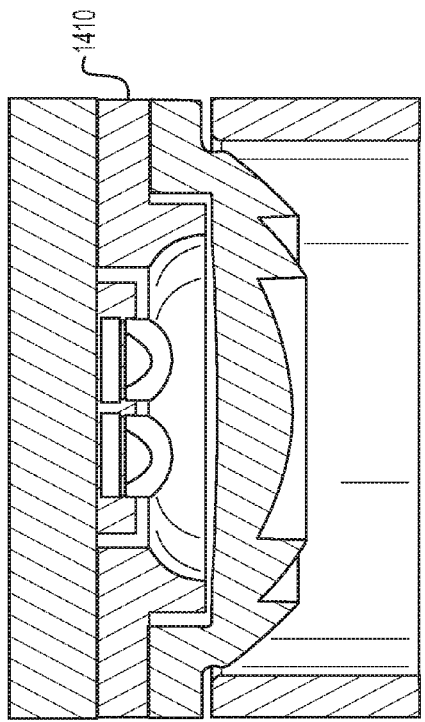
FIGS. 14A, 14B, and 14C provide diagrammatic cross-sections of individual culture wells in different example multiwell microelectrode array (MEA) plates, along with overlying detachable optical stimulation modules, shown coupled to the MEA plates. The multiwell MEA plate lids and LED reflectors in FIGS. 14A, 14B, and 14C are specialized to enhance optical delivery and/or prevent the passage of light between adjacent wells, consistent with certain disclosed embodiments.
Figure 14B:
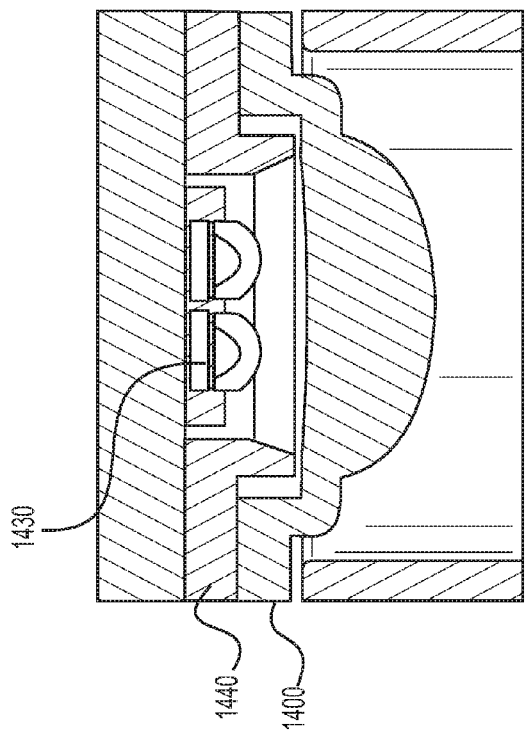
Figure 14C:
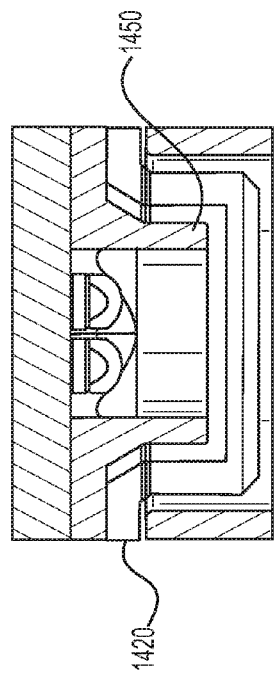

FIG. 14A provides alternate configurations for the lid 1400, reflector 1440, and LEDs 1430, shown in FIG. 13. In FIG. 14A, the lid 1400 is recessed to allow mechanical fitting of the LED reflector, to prevent light escape from the well, and to enable the LEDs and reflector to be moved closer to the target tissue or cells at the bottom of the MEA well. The lid is furthermore shaped with a lens to refract light towards the center of the well, enhancing light delivery to the sample. In 14B the lid is shaped into a Fresnel lens, to provide similar refraction of light, while not extending as far into the well. In 14C the lid is recessed to a greater extent and the LEDs or LED reflector to extend more deeply into the well, offering the potential for improved light delivery or light delivery concentrated towards a region of the target tissue.

It will be apparent to those skilled in the art that various modifications and variations can be made to the disclosed multiwell microelectrode arrays with integrated optical stimulation capabilities and associated methods for using the same. Other embodiments of the present disclosure will be apparent to those skilled in the art from consideration of the specification and practice of the present disclosure. It is intended that the specification and examples be considered as exemplary only, with a true scope of the present disclosure being indicated by the following claims and their equivalents.

What is claimed is:

1. An optical stimulation system, comprising:
a microplate comprising a plurality of wells;
a lid configured to couple to the microplate, wherein at least a portion of the lid contacts the microplate; and
at least one light-emitting element set corresponding to at least one of the plurality of wells and configured to deliver optical stimulation to the at least one well of the plurality of wells, wherein the at least one light-emitting element set is configured to be removably coupled to the lid, and
wherein the lid is configured to modify an optical property of delivered light.

2. The system of claim 1, wherein the microplate is configured to enhance light delivery within each of the plurality of wells or to reduce light bleed-through between two or more of the plurality of wells.

* * * * *